United States Patent
Burke et al.

(10) Patent No.: US 10,718,756 B2
(45) Date of Patent: Jul. 21, 2020

(54) MITOCHONDRIAL APOPTOTIC SENSOR

(71) Applicant: The Regents of the University of California, Oakland, CA (US)

(72) Inventors: Peter Burke, Irvine, CA (US); Ted Pham, Westminster, CA (US); Phi Pham, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/795,924

(22) Filed: Oct. 27, 2017

(65) Prior Publication Data

US 2018/0120300 A1 May 3, 2018

Related U.S. Application Data

(60) Provisional application No. 62/413,659, filed on Oct. 27, 2016.

(51) Int. Cl.
*G01N 33/50* (2006.01)
*G01N 27/414* (2006.01)
*G01N 33/543* (2006.01)

(52) U.S. Cl.
CPC ..... *G01N 33/5079* (2013.01); *G01N 27/4145* (2013.01); *G01N 33/5438* (2013.01)

(58) Field of Classification Search
CPC ........... G01N 33/5079; G01N 33/5438; G01N 27/4145
See application file for complete search history.

(56) References Cited

U.S. PATENT DOCUMENTS

| | | | |
|---|---|---|---|
| 2003/0203365 A1* | 10/2003 | Cao | G01N 33/54353 435/29 |
| 2007/0264634 A1* | 11/2007 | Bock | B82Y 5/00 435/6.11 |
| 2011/0003322 A1* | 1/2011 | Braeken | G01N 33/5058 435/16 |
| 2012/0059156 A1* | 3/2012 | Salemme | B81C 1/00206 530/387.3 |
| 2016/0017416 A1* | 1/2016 | Boyanov | C12Q 1/6825 506/4 |

OTHER PUBLICATIONS

Padmaraj et al., Mitochondrial Membrane Studies Using Impedance Spectroscopy with Parallel pH monitoring, Jul. 2014, PLoS ONE, vol. 9, Issue 7, pp. 1-8. (Year: 2014).*
Pham et al., Cristae remodeling causes acidification detected by integrated graphene sensor during mitochondrial outer membrane permeabilization, Scientific Reports 6:35907 (2016).

* cited by examiner

*Primary Examiner* — Melanie Brown

(57) ABSTRACT

Mitochondria are central to the intrinsic apoptotic pathway of programmed cell death. Commitment to cell death occurs upon mitochondrial outer membrane permeabilization, and dysregulation of this vital apoptotic control point is implicated in various pathologies. Provided herein are novel sensors which can detect, in real time and with great sensitivity, the release of protons from intact mitochondria caused by mitochondrial outer membrane permeabilization. Embodiments include graphene based ion-sensitive field effect transistors.

1 Claim, 2 Drawing Sheets

MITOCHONDRIAL APOPTOTIC SENSOR

CROSS-REFERENCE TO RELATED APPLICATIONS

This application claims the benefit of priority to U.S. Provisional Application Ser. No. 62/413,659 entitled "Apoptotic Sensor," filed Oct. 27, 2016, the contents which are hereby incorporated by reference.

STATEMENT REGARDING FEDERALLY SPONSORED RESEARCH OR DEVELOPMENT

This invention was made with government support under grant numbers AG24373, NS21328, AG13154, and DK73691 awarded by the National Institutes of Health; grant number MURI W911NF-11-1-0024 awarded by the Army Research Office; grant number P200A120220 awarded by the Department of Energy; and grant number DGE-0549479 awarded by the National Science Foundation. The government has certain rights in the invention.

BACKGROUND OF THE INVENTION

Mitochondria are central to the intrinsic apoptotic pathway of programmed cell death. Commitment to cell death occurs upon mitochondrial outer membrane permeabilization (MOMP), which results in the release of cytochrome c (Cyt c) into the cytoplasm, triggering caspases and irreversibly leading to cell death MOMP is regulated by the complex interplay of cell signals and the BCL-2 family of proteins. Dysregulation of this vital apoptotic control point is implicated in various pathologies, including cancer, diabetes, autoimmune conditions, and others, making this checkpoint a promising target for pharmacological intervention.

Accordingly, a means of precisely monitoring and quantifying the MOMP process is desirable. Such a tool would enable the assessment of treatments which act upon BCL-2 and other apoptosis-modulating factors. Currently, MOMP is monitored by optical techniques. Several fluorescence probes are sensitive to mitochondrial membrane potential, such as TMRE, JC-1 and rhodamine 123. Additionally, various immunoassays can ascertain Cyt c concentrations after release. While extremely useful, the prior art tools suffer from various shortcomings. First, the installation of the fluorescent probes into the relevant compartments of the mitochondria can create artifacts not present in intact mitochondria. Secondly, the number of cells required for a detectable signal in optical assays of MOMP is high, for example, with some assays requiring at least 3 or more micrograms of mitochondrial protein.

Accordingly, there is an ongoing need in the art for tools which allow precise monitoring and quantification of the MOMP process without associated artifacts and which are enabled using small samples. Provided herein are novel sensors and associated methods of using such sensors, which sensors and methods provide the art with a means for the facile, sensitive, and accurate assessment of MOMP. Advantageously, the sensors of the invention are highly scalable and enable massively parallel screening of agents for activity which promotes or inhibits the intrinsic apoptotic pathway.

SUMMARY OF THE INVENTION

Provided herein are novel sensors which can detect MOMP in intact mitochondria. The sensors of the invention comprise electronic devices which can quantify, in real time and with great sensitivity, the release of protons from mitochondria, which such fluxes are indicative of the permeabilization of the mitochondrial outer membrane by pro-apoptotic factors.

The scope of the invention extends to methods of using the sensors to detect MOMP, and further includes methods of measuring MOMP while simultaneously visually monitoring the mitochondria.

The scope of the invention further extends to kits that encompass components and agents for making MOMP sensors functionalized with mitochondria.

DETAILED DESCRIPTION OF THE INVENTION

Figure 1:
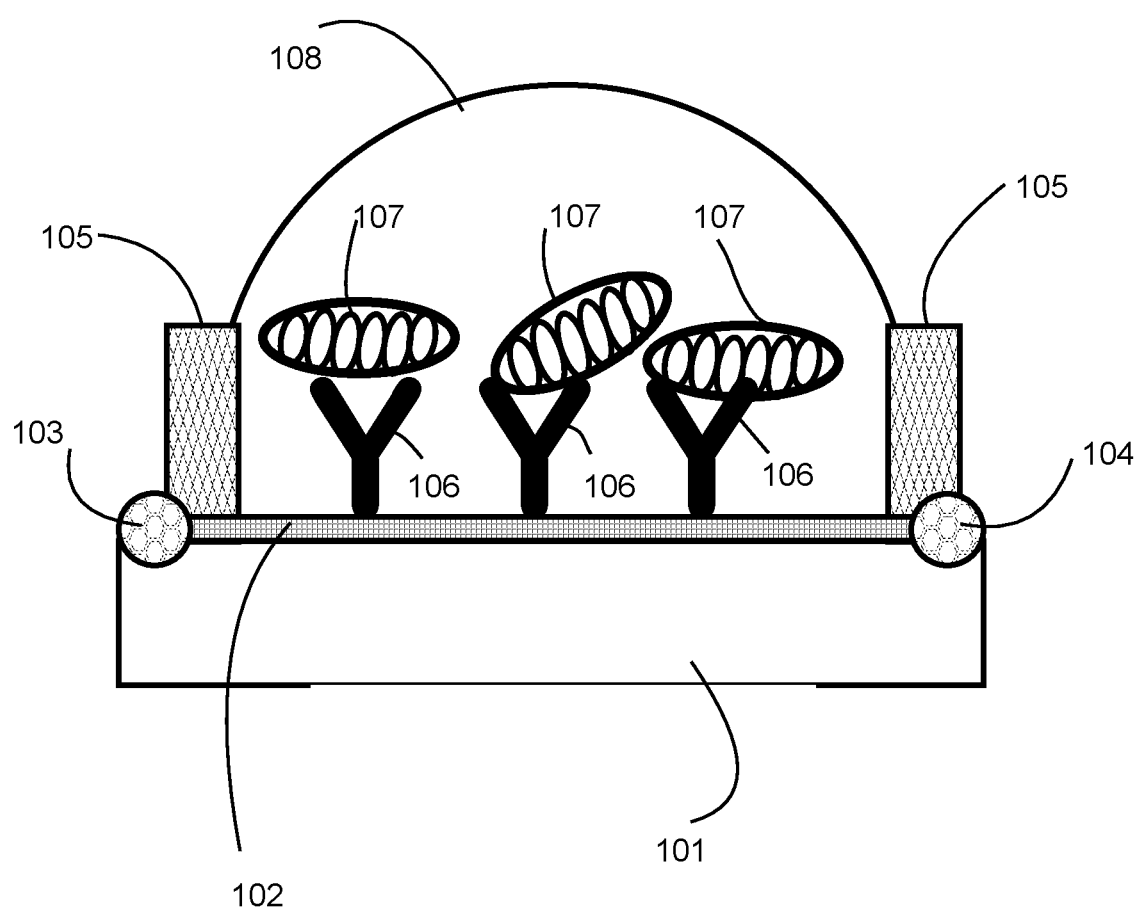
FIG. 1 is a cross-sectional diagram depicting elements of an exemplary sensor of the invention. On a support (101), a layer of graphene is deposited (102). The graphene is in contact with a source electrode (103) and a drain electrode (104). A PDMS containment (105) defines a sample well to contain a droplet of solution (108). The PDMS isolates the electrodes from the solution droplet in the sample well. A plurality of mitochondria (107) are tethered to the graphene substrate by antibodies (106). Current flowing from source to drain can be measured by circuitry (not shown) and the conductance of the gate can be further modulated by a gate electrode (not shown).
Figure 2:
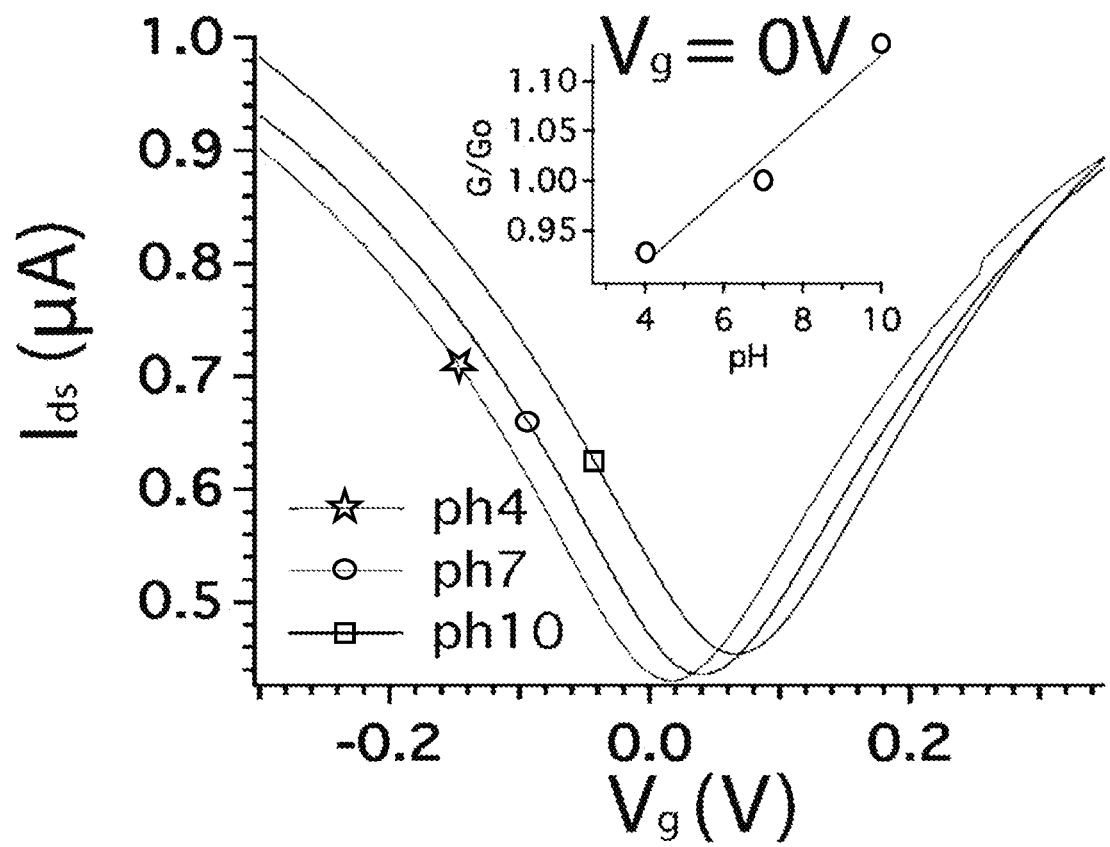
FIG. 2 depicts the source to drain current ($I_{ds}$) vs. gate electrode voltage (Vg). with KCl buffers having different pH values. The inset shows the relative change in conductance of the substrate in different pH buffers, at Vg=0.

In a first aspect, the scope of the invention encompasses electrochemical sensors that can monitor the immediate microenvironment surrounding immobilized mitochondria for changes in pH. Such sensors allow monitoring of proton release from mitochondria, for example, as occurs during MOMP. Accordingly, the sensors provide a means to monitor MOMP in response to various treatments.

In a general embodiment, the invention comprises a device for monitoring pH changes in the microenvironment of mitochondria, the device comprising:
- an electrochemical sensor comprising circuitry for the output of an electrical signal;
- wherein one or more structures comprising a mitochondria-functionalized substrate material is integral to the sensor;
- wherein changes in the electrical properties of the substrate material result in measurable changes to the sensor's signal output; and
- wherein the mitochondria-functionalized substrate material's electrical properties are responsive to the pH of a solution at the substrate surface.

Sensor Configuration

The sensor will comprise an electrochemical sensor comprising circuitry for the output of an electrical signal. The electrochemical sensor of may comprise any assembly of components, such as electrodes, controllers, potentiostats, readout circuitry, sample chambers, and other components, such assemblies being capable of interrogating the electrical properties of the mitochondria-functionalized substrate. The sensors may further comprise elements for signal measurement, storage, processing, and output, including digital memory modules and microprocessors.

The output of the sensor will be an electrical signal. For example, in one embodiment, the output is a current, for example, a current measured between two electrodes. In another embodiment, the output is a voltage.

The sensor is configured with an integral structure (or plurality of structures) wherein the output of the sensor is responsive to changes in one or more electrical properties of the structure. The structure will comprise a substrate material and may further comprise a support. Generally, the electrical properties of the substrate material are responsive to the pH of the solution in contact with the substrate, while the support comprises an electrically inert material (e.g. glass). However, the in alternative implementations, the electrical properties of the support material may be responsive to the pH of solution contacting the support material.

Reference to the pH of solution in contact with the substrate material means the pH of the microenvironment in close proximity to the substrate surface, for example, within nanometers or micrometers of the substrate surface. It will be understood that this localized pH may vary significantly from the bulk pH of the entire solution surrounding the substrate.

The one or more electrical properties of the substrate may comprise any electrical property, for example electrical conductance, resistance, impedance, ionic permeability, or other property related to the material's ability to conduct, resist, sequester, or release charge carriers, such as electrons, holes or protons.

In one implementation, the substrate material comprises graphene. Graphene is highly conductive, and the conductance of graphene is sensitive to the pH of a solution in contact with the graphene. Graphene is electrically sensitive, even at single atom layer thickness, and is easily deposited onto materials and is also easily functionalized. Advantageously, at single atom layer thickness, graphene is highly optically transparent.

The graphene substrate may be deposited onto an electrically neutral or insulating support structure, such as a glass structure, for example planar glass. The graphene substrate may be present in a single layer, or in multiple layers, and may be present in any configuration, for example as one or more ribbons connecting source and drain electrodes.

In an alternative embodiment, the substrate comprises a pH sensitive material other than graphene, for example, gold, polymer electrodes, carbon nanotubes, and other conductor and semi-conductor materials.

In one exemplary implementation, the electrochemical sensor of the invention comprises an ion-sensitive field-effect transistor (ISFET). In this implementation of the invention, the sensor comprises two electrodes, a source and a drain electrode, connected by a conducting body comprising the mitochondria-functionalized substrate material. In one embodiment, the output of the sensor is the current between the source and drain electrodes. Such current will be responsive to the electrical conductance of the conducting body, which in turn is dependent upon pH of the medium contacting the substrate. When the mitochondria associated with the conducting body undergo MOMP, protons released by the permeabilized membranes change the local pH at the substrate surface, altering the conductance of the conducting body, which in turn alters the flow of current between the source and drain electrodes.

The ISFET of the invention may further comprise a gate electrode which can tune the conductance of the conducting body. The gate electrode may comprise, for example, an electrode in contact with the solution surrounding the substrate, such that the solution acts as the gate electrode.

In one embodiment, an increase in $H^+$ concentration around the sensor, for example as caused by MOMP, results in a reduced conductance in the functionalized sensor. In one embodiment, the ISFET comprises a graphene substrate disposed between two silver electrodes, and further comprises an Ag/AgCl gate electrode.

Graphene based ISFETs are known in the art, and may be fabricated and configured, for example, as described in United States Patent Application Publication Number 20150038378, by Cheng and Zhou, entitled "Biocompatible Graphene Sensor"; U.S. Pat. No. 9,618,474 by Van Rooyen et al., entitled "Graphene FET devices, systems, and methods of using the same for sequencing nucleic acids"; and U.S. Pat. No. 8,926,812, by Lee et al., entitled "Cell-based transparent sensor capable of real-time optical observation of cell behavior, method for manufacturing the same and multi-detection sensor chip using the same."

Alternative electrochemical sensor configurations are within the scope of the invention. For example, in one embodiment, the mitochondria-functionalized substrate comprises a first electrode. The sensor further comprises a second electrode comprising a reference electrode. An electrical relationship between the first and second electrodes is interrogated. For example, the current, potential difference, conductance, or other electrical relationships between the functionalized electrode and reference electrode may be assessed. The electronic properties of the first electrode are responsive to pH changes, and this sensitivity to local pH can be used to assess the release of protons from the inner compartments of the mitochondria to the surrounding environment caused by MOMP.

Substrate Functionalization

The substrate material is functionalized with living mitochondria harvested from cells. The mitochondria may be from any species, for example, including humans, animal species, plant species, yeast, mammalian, mouse, etc. Mitochondria may be derived from any cell type of interest, including cancer cells. Mitochondria may be isolated by any means known in the art.

The mitochondria may be treated with a dye or label, or may be transduced to express one or more fluorescent proteins, wherein such dye, label, or fluorescent protein acts as a marker of mitochondrial processes in addition to MOMP. For example, in one embodiment, the mitochondria are treated with a dye that is indicative of membrane potentials within the mitochondria. For example, in one embodiment, the dye is tetramethylrhodamine, ethyl ester (TMRE), thiol-reactive chloromethyl (for example, MITOTRACKER™), or any other dye used to monitor membrane potential.

The mitochondria are tethered to the substrate by one or more linking moieties, such that they are in contact with or in close proximity to the substrate material surface. The linking moieties may comprise a first moiety which binds to the substrate surface and which further binds to a second moiety. The second moiety may comprise a species that binds to the first moiety and which further binds to a mitochondrial surface protein or other chemical entity present on the surface of the mitochondria (a carbohydrate, lipid, or other chemical or organic molecule). One or more intermediate or spacing moieties may be present between the first and second moiety, although in general it is preferred to keep the mitochondria anchored in close proximity to the substrate surface. The moieties may comprise chemical species, carbohydrates, nucleic acids, polypeptides, or any other materials.

In one embodiment, the moiety which binds to the mitochondria comprises an antibody or antigen-binding fragment thereof which is selective for a mitochondrial outer membrane protein. The mitochondrial outer membrane protein may be, for example, TOM20, TOM70, OM45, TOM5, TOM6, TOM22, Bcl-2, Bcl-XL, Fis1, VAMP1B, Fzo1, Porin, or TOM40.

In one embodiment, the substrate is graphene and the mitochondria are tethered to the graphene by a pyrenebutanoic acid-succinimidyl ester (PYR-NHS) and protein conjugate, wherein the protein binds to a mitochondrial outer membrane protein (for example, comprising an antibody). The PYR-NHS binds graphene surfaces with great affinity and also binds the terminal amine of proteins.

The mitochondria may be deposited on the substrate at any desired density. For example, a density of 1000-5000 mitochondria moieties per $mm^2$ of substrate can be used to effectively detect MOMP signals.

Following functionalization, the substrate may be passivated to neutralize any reactive groups or mask exposed substrate material, using materials and methods known in the art. For example, unbound PYR-NHS groups may be treated with ethanolamine. Exposed graphene may be passivated with TWEEN20.

Sensor Arrays

The electrochemical sensors of the invention may comprise arrays of two or more individually substrates. In one embodiment, the individually addressable substrates are present within a single sample chamber. Such individually addressable sections enable functionalization of the sensor with different types of mitochondria. In another embodiment, the individually addressable sections of substrate are present in different sample chambers, allowing for parallel assaying of mitochondria exposed to different agents and/or conditions.

Methods of Use

The scope of the invention encompasses the sensors described above, and further encompasses methods of using such sensors. As described in Example 1, the sensors of the invention provide many advantages, including high sensitivity to pH change and low sensitivity to chemical and biological species in the reaction mixture, and low sensitivity to ROS. Furthermore, the sensor can function using very small mitochondrial samples (for example, in the range of 0.1 μg mitochondrial protein). Furthermore, as described in Example 1, the mitochondria sensors of the invention retain physiologically relevant activity, for example with MOMP induced physiologically by BIM-BH3 peptide, a known activator of BAX/BAK which induces MOMP.

The general method of the invention comprises a method of detecting mitochondrial outer membrane permeabilization, comprising the following steps:
measuring the signal output of an electrochemical sensor of the invention, wherein the
an electrochemical sensor comprises circuitry for the output of an electrical signal;
wherein one or more structures comprising a mitochondria-functionalized substrate material is integral to the sensor;
wherein changes in an electrical property of the substrate material result in a measurable change in the output signal; and
wherein the mitochondria-functionalized substrate's electrical properties are responsive to the pH of solution at the substrate surface; and
wherein a signal associated with lower pH in the solution at the substrate surface is indicative of mitochondrial outer membrane permeabilization.

In one embodiment, the output is a current. In one embodiment, the output is potential difference or voltage. In one embodiment, the output is a depletion curve. In one embodiment, the output is a plot of current vs. gate electrode potential. Such outputs can be associated with the pH of the microenvironment in contact with the substrate by means of a standard curve or other calibration tool. The standard curve can be generated by exposing sensors to solutions of known pH, or by other calibration methods known in the art for electrochemical sensors.

It is understood that the sensors of the invention are operated in contact with a solution, for example present in a well, microfluidic chamber, or other containment, for example, a PDMS containment. Solution volume can vary, for example in the range of 1 microliter to 1 ml. The solution may be a buffer, growth media, or other biocompatible liquid. Generally, the solution will have a carbon source for supporting respiration by the mitochondria. For example, the solution may comprise succinate, for example at 5 mM.

In one embodiment, the measurements of MOMP are performed as the immobilized mitochondria of the sensor are exposed to one or more apoptotic-modulating agents or treatments. For example, in one embodiment, the one or more agents comprises a pro-apoptotic agent. In another embodiment, the one or more agents comprises an anti-apoptotic agent. In another embodiment, the one or more agents comprises a pro-apoptotic agent and a putative anti-apoptotic agent and the ability of the putative anti-apoptotic agent to rescue the mitochondria from apoptosis is assessed. The converse assay is contemplated as well.

In one embodiment, the method of the invention comprises screening methods, wherein arrays of sensors are simultaneously or sequentially assayed with a plurality of putative apoptosis-modulating agents in order to identify agents having an apoptosis-modulating effect. For example, massively parallel screening methods employing hundreds or thousands of sensors may be used to screen molecular libraries.

Simultaneous Visualization

In those implementations wherein the substrate comprises an optically transparent material, such as graphene, the assays of the invention may be performed simultaneously with visualization assays, e.g. fluorescence measurements. Such measurements may comprise any visualization assay, for example fluorescence microscopy by the use of dyes, stains, immunofluorescent assays, and other agents.

In one embodiment, the mitochondria are treated with TMRE, thiol-reactive chloromethyl (for example, MITOTRACKER™), or any other dye used to monitor membrane potential. In such embodiments, MOMP and membrane potential may be monitored simultaneously.

KITS

The sensors of the invention provide a powerful tool for studying MOMP processes in mitochondria. In one embodiment, the scope of the invention encompasses kits, which such kits can be readily distributed to researchers and which can be functionalized with mitochondria by the user at the time of experimentation.

In one embodiment, the kit comprises an electrochemical sensor of the invention, wherein the substrate is not functionalized with mitochondria, but is capable of functionalization with mitochondria. In one embodiment, the kit further comprises one or more agents which facilitate the binding of mitochondria to the substrate surface. For example, such agents may comprise PYR-NHS, antibodies (or fragments thereof) to mitochondrial outer membrane proteins, etc. Additional kit components may include reagents, buffers, agents for the isolation of mitochondria, instructions for using the components of the kits, software for signal interpretation, etc.

EXAMPLES

Example 1

Cristae Remodeling Causes Acidification Detected by Integrated Graphene Sensor During Mitochondrial Outer Membrane Permeabilization

INTRODUCTION

The intrinsic mitochondrial pathway of apoptosis is an important target for pharmacological manipulation for a variety of diseases including cancer. This pathway is regulated by the BCL-2 family proteins[8] and results in the collapse of the inner membrane electrochemical gradient. An early step in the initiation of the intrinsic apoptosis pathway is the mitochondrial outer membrane permeabilization (MOMP). MOMP can be induced by BH3-only proteins such as tBid and BIM and has been proposed to result from the oligomerization of pro-apoptotic BCL-2 family proteins BAX and BAK. BAX and BAK oligomerization activates the metalloprotease, OMA1, to cleave the inner membrane protein OPA1. OPA1 tethers the inner membrane cristae loops together at cristae junctions creating the inter-cristae luminal spaces into which the electron transport chain pumps protons during oxidative phosphorylation (OXPHOS)[10]. Cleavage of OPA1 results in remodeling of the cristae and the opening of the proton-rich cristae luminal spaces. MOMP permits the release of stored intermembrane space pro-apoptotic proteins including cytochrome c (cytc), procaspase-9, and Smac/DIABLO into the cytoplasm, causing activation of caspases and the commitment to cell death.

It has been reported that the cytosol becomes acidified soon after the intrinsic apoptosis pathway is activated. However, there has not been a method to quantify and thus understand the molecular and physiological basis of this phenomenon.

Here, is presented an electronic method to detect extra-mitochondrial pH of isolated mitochondria, based on tethering the mitochondria to one-atom thin graphene. The mitochondria are tethered via graphene bound antibodies which recognize the mitochondrial outer membrane protein, TOM20. Graphene is an excellent conductor and changes in the pH surrounding the mitochondria can change the graphene conductance and be detected electrically. Being optically transparent, the graphene layer also permits optical interrogation of the mitochondria concurrent with analysis of ionic changes. Hence, the system permits the simultaneous monitoring of changes in extra-mitochondrial pH through graphene conductance and inner membrane potential ($\Delta\psi_m$) using the potentiometric fluorescent dye tetramethylrhodamine ethyl ester perchlorate (TMRE).

METHODS

Graphene Transfer and Device Fabrication

Graphene was transferred on to glass substrates using a modified protocol described in Wang, Y. Y. & Burke, P. J. A large-area and contamination-free graphene transistor for liquid-gated sensing applications. *Appl. Phys. Lett.* 103, 52103 (2013). Briefly, a 5 cm×5 cm copper foil containing CVD grown single-layer graphene on one side was cut into 0.6 cm×1.0 cm sheets. The side of the sheet containing graphene was pressed lightly against a block of pre-cured PDMS. The Cu-graphene-PDMS structure was then placed and left floating in a Cu-etchant bath (50 mg/ml ammonium persulfate in DI water). After the copper was completely etched away, the graphene-PDMS structure was washed three times with DI $H_2O$ for one hour to eliminate any residual ions from the copper etching step. The wet PDMS/graphene block was then pressed against a 1-mm thick glass slide that had been cleaned for one hour with 1:3 (v/v) $H_2O_2$:$H_2SO_4$ solution. The glass-graphene-PDMS slide was kept under a slight pressure overnight to promote graphene-glass adhesion and allow the interfacial water to evaporate. When the device was completely dry, the PDMS was carefully peeled off, leaving large-area single-layer graphene on the glass slide.

Following graphene transfer, an experimental chamber was fabricated on top of the graphene, drain and source electrodes to measure the graphene in-plane conductance were fabricated, and the electrodes were insulated from the experimental liquid. To accomplish these goals, a simple, freshly cured PDMS slab with an inner cut-out was placed directly on top of the graphene and served as the experimental chamber. Additionally, due to having narrow width, the PDMS slab, although covering most graphene area, still left some exposed graphene where quick-dry silver paste was painted to establish electrical connection.

Graphene Functionalization

After the silver-paste electrodes were completely dry, graphene functionalization was carried out using a series of solution deposition, incubation and wash. Each step in the series employed 50 μL volume. First, 3.81 mg of pyrene-NHS was mixed with 2 mL dimethylformamide (DMF), and added to the PDMS chamber of each graphene device. Incubation with pyrene-NHS ensued for one hour at room temperature. The device was then washed sequentially with fresh DMF, DI water and PBS pH 7.2. Anti-TOM20 antibody solution was added at 33.3 μg/mL concentration and incubated overnight at 4° C. After two wash steps with PBS then DI $H_2O$, 0.1 M ethanolamine diluted in DI $H_2O$ was added and incubated for one hour at room temperature then washed with DI $H_2O$. The next incubation with 0.1% TWEEN-20 was set for one hour at room temperature to deactivate the exposed graphene area by preventing unspecific protein adsorption. The functionalization scheme was partially adapted from Huang, Y., Dong, X., Liu, Y., Li, L.-J. & Chen, P. Graphene-based biosensors for detection of bacteria and their metabolic activities. *J. Mater. Chem.* 21, 12358 (2011). Finally, the devices were washed with DI $H_2O$ then KCl buffer for immediate use.

CELL CULTURE AND MITOCHONDRIA ISOLATION

Cell Preparation

The mammalian cell lines: HeLa and RS4;11 (American Type Culture Collection) were maintained in the log growth phase using the appropriate tissue culture protocols for adherent and suspension cells, respectively. On the days of the experiment, $10^7$ cells were typically harvested for mitochondria isolation.

Mitochondria Staining

Before isolation, the confluent cells were stained with 100 nM MITOTRACKER™ Green FM and 40 nM TMRE for 1 hour. Subsequent isolation steps used solutions with 40 nM TMRE because TMRE is a potentiometric dye, which fluctuates in and out of the mitochondria depending on their inner membrane potential. 40 nM was determined as the optimal concentration.

Mitochondria Isolation

An isolation buffer containing 225 mM mannitol, 75 mM sucrose, 0.5 mM EGTA, 20 mM HEPES, 0.5% (w/v) BSA, 1× protease inhibitor, pH 7.2 with 1 M KOH was used. The stock isolation buffer was prepared without BSA and the protease inhibitor and stored at 4° C. Mitochondria from the cultured cells were isolated using differential centrifugation. After collection, the cells were transferred to a glass homogenization tube in 3 mL of complete isolation buffer and homogenized with 30 strokes on ice for HeLa cells and 40 strokes for RS4;11. The cells were then transferred into 2-ml tubes and centrifuged at a low speed of 2000×g for 4 min at 4° C. The resulting supernatant was collected and centrifuged at a high speed of 12,000×g×10 min at 4° C. After this step, the supernatant as well as the light-colored fluffy sediment containing damaged mitochondria were aspirated and the resulting pellet was resuspended in KCl buffer (140 mM KCl, 2 mM $MgCl_2$, 10 mM NaCl, 0.5 mM EGTA, 0.5 mM $KH_2PO_4$, 2 mM HEPES, 5 mM succinate, 2 μM rotenone, pH 7.2 adjusted with KOH). However, for mitochondria protein analysis, the mitochondria were resuspended in KCl buffer without EGTA. The protein analysis was done with BCA assay kit. A typical mitochondrial preparation with this protocol exhibits a respiratory control ratio of 3.1.

Fluorescence Measurement

Using an inverted microscope with two LED excitation sources (490 nm & 565 nm the red and green fluorescence signals from the MITOTRACKER™ and TMRE were visualized with 20× objective at 200 μm×300 μm, exposure time one second. To process and analyze the images, ImageJ software was used. For the entire field of view analysis, fluorescence intensity was measured from the field of view. In contrast, for single mitochondrion analysis, regions of interest enclosing the mitochondria were defined and three more identical copies of that region of interest were used to define the background noise. Fluorescence signal of the mitochondria was assigned as the measured signal subtracting the noise average.

Experimental Design and Electrical Measurement

After mitochondria isolation, about 6 μg of mitochondrial protein of isolated mitochondria was loaded to a graphene device and incubated for 15 min at room temperature. Following two gentle washes with KCl buffer, the device was secured on the microscope stage, and the focus was adjusted. Electrical contacts were attached to the drain and source terminals of the devices using nickel (type) probes. The gate electrode was a Ag/AgCl electrode. When both optical focus and electrical connection were satisfactory, fluorescent images and $I_{ds}$ versus $V_g$ curve, were collected. The electrical measurement of $I_{ds}$ versus time and the fluorescence time-lapse measurement of TMRE signal were collected. The electrical data sampling rate was 200 ms/point. In contrast, fluorescence images were taken once every 5 s for the experiments with CCCP or every 2 min for the experiments with BIM-BH3.

The starting volume of the chamber was 45 μL. During the experiment, 4.5 μL of the appropriate experimental substrate was added to achieve its final concentration. Extreme care was taken not to disturb the gate electrode.

Control experiments were carried out in a similar manner with the only difference being the lack of isolated mitochondria. Software was used to analyze all electrical data and the fluorescence data that were exported from ImageJ software. The KCl buffer contained 5 mM succinate as a carbon source for the mitochondria, facilitating the maintenance of $\Delta\psi_m$. Since the electrons derived from succinate doesn't go through complex I, rotenone was added. The succinate and rotenone were intended to limit ROS production by complex I. ADP was omitted from the respiration buffer to avoid ATP synthase activation. This maximized $\Delta\psi_m$, maintaining a functional but not functioning ETC, and also limiting ROS production by complex I.

RESULTS

The density of mitochondria attachment was calculated to be 4237±279 mitochondria/$mm^2$ for HeLa cells and 1418/$mm^2$±328 for RS4:11 cells; the sample sizes were three. It was computed that a device would have approximately 85,000 mitochondria at the upper limit. Assuming 1 μg of mitochondrial protein yields $10^6$ particles of isolated mitochondria, after washing, the device would require at most 0.1 μg of mitochondrial protein.

The sensors were tested using a variety of agents to alter mitochondrial membranes. It was observed that the devices are pH-sensitive, but insensitive to CCCP, BIM-BH3, and cytc, and are only mildly sensitive to succinate and $K^+$ ions. Further, it was observed that CCCP causes ΔΨm to decrease and buffer pH to increase. It was also observed that BIM-BH3-induced MOMP causes oligomycin-independent buffer acidification (decreasing $pH_{buffer}$) and $\Delta\Psi_m$ decay. Also, exogenous cytc blocks buffer acidification and rescues ΔΨm after BIM-BH3 induced MOMP. Results were consistent with the expected effects of the applied agents.

Results were benchmarked against a conventional pH meter, and were found to be consistent. However, the conventional pH meter had barely sufficient pH resolution (0.01 pH) and a slow response time, as compared to the integrated graphene detectors.

Herein is demonstrated a novel system for assessing functional changes in mammalian mitochondria. The acute sensitivity of the devices permitted the dissection accurate and high resolution of alterations in the mitochondrial membrane status during various mitochondrial processes such as uncoupled depolarization of OXPHOS and the induction of the intrinsic pathway of apoptosis initiated by the pro-apoptotic peptide BIM-BH3.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of detecting mitochondrial outer membrane permeabilization, comprising performing the step of measuring the signal output of an electrochemical sensor; wherein the electrochemical sensor comprises circuitry for the output of an electrical signal;

wherein one or more structures comprising a mitochondria-functionalized graphene substrate in a droplet of solution is integral to the sensor;

wherein changes in an electrical property of the graphene substrate result in a measurable change in the output signal;

wherein the mitochondria-functionalized graphene substrate's electrical property is responsive to the pH of the solution at the graphene surface; and performing the step of comparing the sensor output to a standard curve associating sensor output to pH in order to calculate the pH of the solution;

wherein the measured pH of the solution at the graphene layer surface is indicative of mitochondrial outer membrane permeabilization status; and wherein the graphene substrate of the electrochemical sensor is optically transparent; and the method comprises the additional step of visually monitoring the mitochondria present on the graphene substrate during the measurement of the output signal of the electrochemical sensor.

* * * * *